(12) United States Patent
Crowley

(10) Patent No.: US 7,511,151 B2
(45) Date of Patent: Mar. 31, 2009

(54) SUBSTITUTED PYRIDYLOXYALKYLAMIDES AND THEIR USE AS FUNGICIDES

(75) Inventor: Patrick Jelf Crowley, Bracknell (GB)

(73) Assignee: Syngenta Limited (GB)

( * ) Notice: Subject to any disclaimer, the term of this patent is extended or adjusted under 35 U.S.C. 154(b) by 540 days.

(21) Appl. No.: 10/536,461

(22) PCT Filed: Oct. 23, 2003

(86) PCT No.: PCT/GB03/04547

§ 371 (c)(1),
(2), (4) Date: May 25, 2005

(87) PCT Pub. No.: WO2004/048337

PCT Pub. Date: Jun. 10, 2004

(65) Prior Publication Data

US 2006/0148859 A1    Jul. 6, 2006

(30) Foreign Application Priority Data

Nov. 26, 2002  (GB)  ........................ 0227554.3

(51) Int. Cl.
C07D 213/63  (2006.01)
A01N 43/40   (2006.01)

(52) U.S. Cl. ........................ 546/291; 514/277
(58) Field of Classification Search ............. 514/277; 546/291

See application file for complete search history.

(56) References Cited

U.S. PATENT DOCUMENTS

| | | |
|---|---|---|
| 3,272,844 A | 9/1966 | Easton et al. |
| 4,049,423 A | 9/1977 | Baker et al. |
| 4,062,977 A | 12/1977 | Baker et al. |
| 4,070,486 A | 1/1978 | Baker et al. |
| 4,083,867 A | 4/1978 | Baker et al. |
| 4,116,677 A | 9/1978 | Walker et al. |
| 4,146,387 A | 3/1979 | Thiele |
| 4,154,849 A | 5/1979 | Walker et al. |
| 4,168,319 A | 9/1979 | Walker et al. |
| 4,784,682 A | 11/1988 | Forster et al. |
| 6,048,860 A | 4/2000 | Farrar et al. |
| 6,090,815 A | 7/2000 | Muramatsu et al. |
| 6,156,769 A | 12/2000 | Farrar et al. |
| 2005/0065032 A1 | 3/2005 | Whittingham et al. |
| 2006/0019973 A1 | 1/2006 | Salmon et al. |
| 2006/0058397 A1 | 3/2006 | Salmon |
| 2006/0140997 A1 | 6/2006 | Pitterna et al. |
| 2006/0194763 A1 | 8/2006 | Salmon et al. |
| 2006/0217346 A1* | 9/2006 | Crowley et al. ............. 514/63 |
| 2007/0042996 A1* | 2/2007 | Crowley et al. ............. 514/63 |

FOREIGN PATENT DOCUMENTS

| | | |
|---|---|---|
| CA | 1132580 A | 9/1982 |
| DE | 2731960 A1 | 2/1978 |
| DE | 2948095 A1 | 6/1981 |
| DE | 3702964 A1 | 8/1988 |
| EP | 0001721 | 5/1979 |
| EP | 0010298 A1 | 4/1980 |
| EP | 0751120 A2 | 1/1997 |
| EP | 0940392 A1 | 9/1999 |
| FR | 2359816 A1 | 2/1978 |
| JP | 06186702 A | 7/1994 |
| JP | 201089453 A | 4/2001 |
| JP | 04021677 A | 1/2004 |
| WO | 9933810 | 7/1999 |
| WO | 03048128 | 6/2003 |
| WO | 2004047538 A1 | 6/2004 |
| WO | 2004048316 A1 | 6/2004 |
| WO | 2004048337 A1 | 6/2004 |
| WO | 2004052100 A1 | 6/2004 |
| WO | 2004108663 A1 | 12/2004 |
| WO | 2004108694 A1 | 12/2004 |
| WO | 2006058699 A1 | 6/2006 |
| WO | 2006058700 A1 | 6/2006 |

OTHER PUBLICATIONS

F. Z. Dorwald "Side Reactions in Organic Synthesis: A Guide to Successful Synthesis Design" 2005 Wiley-VCH Verlag GmbH & KGaA, Wienheim.*

* cited by examiner

*Primary Examiner*—Rita J Desai
*Assistant Examiner*—John Mabry
(74) *Attorney, Agent, or Firm*—James Cueva

(57) ABSTRACT

Fungicidal compounds of the general formula (1), or the corresponding pyridine N-oxide, wherein X, Y, $R_1$, $R_2$, $R_3$, $R_4$ and $R_5$ are as defined in the description.

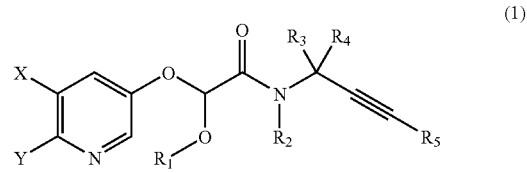

(1)

3 Claims, No Drawings

SUBSTITUTED PYRIDYLOXYALKYLAMIDES AND THEIR USE AS FUNGICIDES

This application is a 371 of International Application No. PCT/GB2003/004547 filed Oct. 23, 2003, which claims priority to GB 0227554.3, filed Nov. 26, 2002, the contents of which are incorporated herein by reference.

This invention relates to novel N-alkynyl-2-(substituted pyridyloxy)alkylamides, to processes for preparing them, to compositions containing them and to methods of using them to combat fungi, especially fungal infections of plants.

Certain pyridyl- and pyrimidinyloxy(thio)alkanoic acid amide derivatives are described in, for example, WO 99/33810 and U.S. Pat. No. 6,090,815 together with their use as agricultural and horticultural fungicides. Certain N-alkynyl-2-(substituted phenoxy)-alkylamides are described in U.S. Pat. No. 4,116,677 as being useful as herbicides. Others are described in U.S. Pat. No. 4,168,319 as being useful as mildewicides. Several N-dimethyl-propynyl-α-methoxy- and α-ethoxy-α-(substituted phenoxy)acetamides are described in U.S. Pat. No. 4,062,977 for use as miticides and the compound N-dimethylpropynyl-α-methoxy-α-(3,5-dimethylphenoxy)acetamide is described in U.S. Pat. No. 4,083,867 for use as a herbicide.

The present invention is concerned with the provision of particular N-alkynyl-2-(substituted pyridyloxy)alkylamides for use as plant fungicides.

Thus according to the present invention there is provided a compound of the general formula (1):

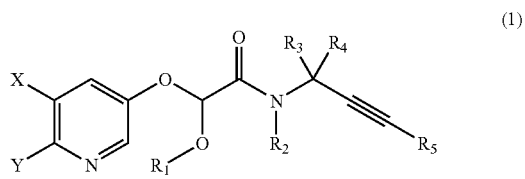

or the corresponding pyridine N-oxide, wherein

X and Y are independently halo (e.g. fluoro, chloro and bromo), $C_{1-4}$ alkyl (e.g. methyl), halo($C_{1-4}$)alkyl (e.g. trifluoromethyl), $C_{2-4}$ alkenyl (e.g. vinyl), halo($C_{2-4}$)alkenyl, $C_{2-4}$alkynyl (e.g. ethynyl), halo($C_{2-4}$)alkynyl, $C_{1-4}$ alkoxy (e.g. methoxy), halo($C_{1-4}$)alkoxy (e.g. trifluoromethoxy), —S(O)$_n$($C_{1-4}$)alkyl where n is 0, 1 or 2 and the alkyl group is optionally substituted with fluoro (e.g. methylthio, methylsulphinyl, methylsulphonyl, trifluoromethylthio and trifluoromethylsulphonyl), —OSO$_2$($C_{1-4}$)alkyl where the alkyl group is optionally substituted with fluoro (e.g. trifluoromethylsulphonyloxy), cyano, nitro, $C_{1-4}$ alkoxycarbonyl (e.g. methoxycarbonyl), —CONR'R", —COR', —NR'COR", —NR'CO$_2$R''' where R' and R" are independently H or $C_{1-4}$ alkyl and R''' is $C_{1-4}$ alkyl (e.g. acetyl, —NHCOCH$_3$ and —NHCO$_2$CH$_3$), or optionally substituted phenyl, or Y is H;

$R_1$ is a straight-chain $C_{1-4}$ alkyl group (e.g. methyl, ethyl, n-propyl and n-butyl);

$R_2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy;

$R_3$ and $R_4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R_3$ and $R_4$ join with the carbon atom to which they are attached to form a 3 or 4 membered carbocyclic ring optionally containing one O, S or N atom and optionally substituted with halo or $C_{1-4}$ alkyl; and $R_5$ is H, $C_{1-4}$ alkyl or $C_{3-6}$ cycloalkyl in which the alkyl or cycloalkyl group is optionally substituted with halo, hydroxy, $C_{1-6}$ alkoxy, cyano, $C_{1-4}$ alkylcarbonyloxy, aminocarbonyloxy, mono- or di($C_{1-4}$)alkylaminocarbonyloxy, —S(O)$_n$($C_{1-6}$)alkyl where n is 0, 1 or 2, triazolyl (e.g. 1,2,4-triazol-1-yl), tri($C_{1-4}$)alkylsilyloxy, optionally substituted phenoxy, optionally substituted thienyloxy, optionally substituted benzyloxy or optionally substituted thienylmethoxy, or $R_5$ is optionally substituted phenyl, optionally substituted thienyl or optionally substituted benzyl;

in which the optionally substituted phenyl and thienyl rings of the X, Y and $R_5$ values are optionally substituted with one, two or three substituents selected from halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, halo($C_{1-4}$)alkylthio, hydroxy($C_{1-4}$)-alkyl, $C_{1-4}$alkoxy($C_{1-4}$)alkyl, $C_{3-6}$ cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R'', —NHCOR''', —NHCONR'''R'', —CONR'''R'', —SO$_2$R''', —OSO$_2$R''', —COR''', —CR'''=NR'' or —N=CR'''R'', in which R''' and R'' are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

The compounds of the invention contain at least one asymmetric carbon atom (and at least two when $R_3$ and $R_4$ are different) and may exist as enantiomers (or as pairs of diastereoisomers) or as mixtures of such. However, these mixtures may be separated into individual isomers or isomer pairs, and this invention embraces such isomers and mixtures thereof in all proportions. It is to be expected that for any given compound, one isomer may be more fungicidally active than another.

Except where otherwise stated, alkyl groups and alkyl moieties of alkoxy, alkylthio, etc., suitably contain from 1 to 4 carbon atoms in the form of straight or branched chains. Examples are methyl, ethyl, n- and iso-propyl and n-, sec-, iso- and tert-butyl. Where alkyl moieties contain 5 or 6 carbon atoms, examples are n-pentyl and n-hexyl.

Alkenyl and alkynyl moieties also suitable contain from 2 to 4 carbon atoms in the form of straight or branched chains. Examples are allyl, ethynyl and propargyl.

Halo includes fluoro, chloro, bromo and iodo. Most commonly it is fluoro, chloro or bromo and usually fluoro or chloro.

The substituent X is typically fluoro, chloro, bromo, methyl, cyano, phenyl, acetyl, vinyl, ethynyl, methoxy, trifluoromethoxy, methylthio, methylsulphinyl, methylsulphonyl, trifluoromethylthio, methoxycarbonyl, methylcarbonylamino or methoxycarbonylamino. Of particular interest are compounds where X is chloro or bromo and especially chloro.

Y is typically H, halo (e.g. fluoro or chloro) or methyl, but preferably it is H.

$R_1$ is methyl, ethyl, n-propyl or n-butyl. Methyl and ethyl are preferred values of $R_1$.

Typically $R_2$ is H and at least one, but preferably both of $R_3$ and $R_4$ are methyl. When one of $R_3$ and $R_4$ is H, the other may be methyl, ethyl or n- or iso-propyl. When one of $R_3$ and $R_4$ is methyl, the other may be H or ethyl but is preferably also methyl. $R_2$ also includes $C_{1-4}$ alkoxymethyl and benzyloxymethyl in which the phenyl ring of the benzyl group optionally carries an alkoxy substituent, e.g. a methoxy substituent. Such values of $R_2$ provide compounds of formula (1) that are believed to be pro-pesticidal compounds.

Typically $R_5$ is H, methyl, hydroxymethyl, methoxymethyl, 1-methoxyethyl, tert-butyldimethylsilyloxymethyl, 3-cyanopropyl, 3-(1,2,4-triazol-1-yl)propyl, 3-methylthiopropyl, 3-methanesulphinylpropyl or 3-methanesulphonylpropyl. Of particular interest are compounds where $R_5$ is methyl, methoxymethyl or cyanopropyl.

In one aspect, the invention provides a compound of the general formula (1) wherein X and Y are independently halogen, $C_{1-4}$ alkyl, $C_{2-4}$ alkenyl, $C_{2-4}$ alkynyl, optionally substituted phenyl, cyano, or —COR' where R' is H or $C_{1-4}$ alkyl, or Y is H; $R_1$ is a straight-chain $C_{1-4}$ alkyl group; $R_2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy, $R_3$ and $R_4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R_3$ and $R_4$ join with the carbon atom to which they are attached to form a 3 or 4 membered carbocyclic ring optionally containing one O, S or N atom and optionally substituted with halo or $C_{1-4}$ alkyl; and $R_5$ is H, $C_{1-4}$ alkyl or $C_{3-6}$ cycloalkyl in which the alkyl or cycloalkyl group is optionally substituted with halo, hydroxy, $C_{1-6}$ alkoxy, $C_{1-6}$ alkylthio, cyano, $C_{1-4}$ alkylcarbonyloxy, aminocarbonyloxy or mono- or di($C_{1-4}$)alkylaminocarbonyloxy, tri($C_{1-4}$)alkylsilyloxy, optionally substituted phenoxy, optionally substituted thienyloxy, optionally substituted benzyloxy or optionally substituted thienylmethoxy, or $R_5$ is optionally substituted phenyl, optionally substituted thienyl or optionally substituted benzyl, in which the optionally substituted phenyl and thienyl rings of the X, Y and $R_5$ values are optionally substituted with one, two or three substituents selected from halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$alkylthio, halo($C_{1-4}$)alkylthio, hydroxy($C_{1-4}$)alkyl, $C_{1-4}$alkoxy($C_{1-4}$)alkyl, $C_{3-6}$ cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R'', —NHCOR''', —NHCONR'''R'', —CONR'''R'', —SO$_2$R''', —OSO$_2$R''', —COR''', —CR'''=NR'' or —N=CR'''R'', in which R''' and R'' are independently hydrogen, $C_{1-4}$ alkyl, halo($C_{1-4}$)alkyl, $C_{1-4}$ alkoxy, halo($C_{1-4}$)alkoxy, $C_{1-4}$alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

In another aspect, the invention provides a compound of the general formula (1) wherein X is chloro or bromo; Y is H; $R_1$ is methyl, ethyl, n-propyl, n-butyl; $R_2$ is H; $R_3$ and $R_4$ are both methyl; and $R_5$ is H, methyl, hydroxymethyl, methoxymethyl, 1-methoxyethyl, tert-butyldimethylsilyloxymethyl, 3-cyanopropyl, 3-(1,2,4-triazol-1-yl)propyl, 3-methylthiopropyl, 3-methanesulphinylpropyl and 3-methanesulphonylpropyl. Preferably $R_1$ is methyl or ethyl. Preferably $R_5$ is methyl, methoxymethyl or cyanopropyl.

Compounds that form part of the invention are illustrated in Tables 1 to 28 below.

The compounds in Table 1 are of the general formula (1) where $R_1$ is ethyl, $R_2$ is H, $R_3$ and $R_4$ are both methyl, $R_5$ is methyl and X and Y have the values given in the table.

TABLE 1

| Compound No | X | Y |
|---|---|---|
| 1 | Cl | H |
| 2 | F | H |
| 3 | Br | H |
| 4 | $CH_3$ | H |
| 5 | Cl | Cl |
| 6 | Cl | $CH_3$ |
| 7 | CN | H |
| 8 | $C_6H_5$ | H |
| 9 | $CH_3CO$ | H |
| 10 | HC≡C | H |
| 11 | $CH_2$=CH | H |
| 12 | Cl | F |
| 13 | Br | F |
| 14 | F | F |
| 15 | Cl | $CH_3$ |
| 16 | CN | F |
| 17 | CN | Cl |
| 18 | $CH_3O$ | H |
| 19 | $CF_3O$ | H |
| 20 | $CH_3S$ | H |
| 21 | $CH_3SO$ | H |
| 22 | $CH_3SO_2$ | H |
| 23 | $CF_3S$ | H |
| 24 | $CF_3SO$ | H |
| 25 | $CF_3SO_2$ | H |
| 26 | $CH_3O_2C$ | H |
| 27 | $CH_3CONH$ | H |
| 28 | $CH_3O_2CNH$ | H |

Table 2

Table 2 consists of 28 compounds of the general formula (1), where $R_1$ is methyl, $R_2$ is hydrogen, $R_3$ and $R_4$ are both methyl, $R_5$ is methyl and X and Y have the values listed in Table 1. Thus compound 1 of Table 2 is the same as compound 1 of Table 1 except that in compound 1 of Table 2 $R_1$ is methyl instead of ethyl. Similarly, compounds 2 to 28 of Table 2 are the same as compounds 2 to 28 of Table 1, respectively, except that in the compounds of Table 2 $R_1$ is methyl instead of ethyl.

Table 3

Table 3 consists of 28 compounds of the general formula (1), where $R_1$ is n-propyl, $R_2$ is hydrogen, $R_3$ and $R_4$ are both methyl, and $R_5$ is methyl and X and Y have the values listed in Table 1. Thus compound 1 of Table 3 is the same as compound 1 of Table 1 except that in compound 1 of Table 3 $R_1$ is n-propyl instead of ethyl. Similarly, compounds 2 to 28 of Table 3 are the same as compounds 2 to 28 of Table 1, respectively, except that in the compounds of Table 3 $R_1$ is n-propyl instead of ethyl.

Table 4

Table 4 consists of 28 compounds of the general formula (1), where $R_1$ is n-butyl, $R_2$ is hydrogen, $R_3$ and $R_4$ are both methyl, $R_5$ is methyl and X and Y have the values listed in Table 1. Thus compound 1 of Table 4 is the same as compound 1 of Table 1 except that in compound 1 of Table 4 $R_1$ is n-butyl instead of ethyl. Similarly, compounds 2 to 28 of Table 4 are the same as compounds 2 to 28 of Table 1, respectively, except that in the compounds of Table 4 $R_1$ is n-butyl instead of ethyl.

Table 5

Table 5 consists of 28 compounds of the general formula (1), where $R_1$ is ethyl, $R_2$ is hydrogen, $R_3$ and $R_4$ are both methyl, $R_5$ is H and X and Y have the values listed in Table 1. Thus compound 1 of Table 5 is the same as compound 1 of Table 1 except that in compound 1 of Table 5 $R_5$ is H instead of methyl. Similarly, compounds 2 to 28 of Table 5 are the same as compounds 2 to 28 of Table 1, respectively, except that in the compounds of Table 5 $R_5$ is H instead of methyl.

Table 6

Table 6 consists of 28 compounds of the general formula (1), where $R_1$ is methyl, $R_2$ is hydrogen, $R_3$ and $R_4$ are both methyl, $R_5$ is H and X and Y have the values listed in Table 1. Thus compound 1 of Table 6 is the same as compound 1 of Table 2 except that in compound 1 of Table 6 $R_5$ is H instead of methyl. Similarly, compounds 2 to 28 of Table 6 are the same as compounds 2 to 28 of Table 2, respectively, except that in the compounds of Table 6 $R_5$ is H instead of methyl.

Table 7

Table 7 consists of 28 compounds of the general formula (1), where $R_1$ is n-propyl, $R_2$ is hydrogen, $R_3$ and $R_4$ are both methyl, and $R_5$ is H and X and Y have the values listed in Table 1. Thus compound 1 of Table 7 is the same as compound 1 of Table 3 except that in compound 1 of Table 7 $R_5$ is H instead of methyl. Similarly, compounds 2 to 28 of Table 7 are the same as compounds 2 to 28 of Table 3, respectively, except that in the compounds of Table 7 $R_5$ is H instead of methyl.

Table 8

Table 8 consists of 28 compounds of the general formula (1), where $R_1$ is n-butyl, $R_2$ is hydrogen, $R_3$ and $R_4$ are both methyl, $R_5$ is H and X and Y have the values listed in Table 1. Thus compound 1 of Table 8 is the same as compound 1 of Table 4 except that in compound 1 of Table 8 $R_5$ is H instead of methyl. Similarly, compounds 2 to 28 of Table 8 are the same as compounds 2 to 28 of Table 4, respectively, except that in the compounds of Table 8 $R_5$ is H instead of methyl.

Table 9

Table 9 consists of 28 compounds of the general formula (1), where $R_1$ is ethyl, $R_2$ is hydrogen, $R_3$ and $R_4$ are both methyl, $R_5$ is hydroxymethyl and X and Y have the values listed in Table 1. Thus compound 1 of Table 9 is the same as compound 1 of Table 1 except that in compound 1 of Table 9 $R_5$ is hydroxymethyl instead of methyl. Similarly, compounds 2 to 28 of Table 9 are the same as compounds 2 to 28 of Table 1, respectively, except that in the compounds of Table 9 $R_5$ is hydroxymethyl instead of methyl.

Table 10

Table 10 consists of 28 compounds of the general formula (1), where $R_1$ is methyl, $R_2$ is hydrogen, $R_3$ and $R_4$ are both methyl, $R_5$ is hydroxymethyl and X and Y have the values listed in Table 1. Thus compound 1 of Table 10 is the same as compound 1 of Table 2 except that in compound 1 of Table 10 $R_5$ is hydroxymethyl instead of methyl. Similarly, compounds 2 to 28 of Table 10 are the same as compounds 2 to 28 of Table 2, respectively, except that in the compounds of Table 10 $R_5$ is hydroxymethyl instead of methyl.

Table 11

Table 11 consists of 28 compounds of the general formula (1), where $R_1$ is n-propyl, $R_2$ is hydrogen, $R_3$ and $R_4$ are both methyl, and $R_5$ is hydroxymethyl and X and Y have the values listed in Table 1. Thus compound 1 of Table 11 is the same as compound 1 of Table 3 except that in compound 1 of Table 11 $R_5$ is hydroxymethyl instead of methyl. Similarly, compounds 2 to 28 of Table 11 are the same as compounds 2 to 28 of Table 3, respectively, except that in the compounds of Table 11 $R_5$ is hydroxymethyl instead of methyl.

Table 12

Table 12 consists of 28 compounds of the general formula (1), where $R_1$ is n-butyl, $R_2$ is hydrogen, $R_3$ and $R_4$ are both methyl, $R_5$ is hydroxymethyl and X and Y have the values listed in Table 1. Thus compound 1 of Table 12 is the same as compound 1 of Table 4 except that in compound 1 of Table 12 $R_5$ is hydroxymethyl instead of methyl. Similarly, compounds 2 to 28 of Table 12 are the same as compounds 2 to 28 of Table 4, respectively, except that in the compounds of Table 12 $R_5$ is hydroxymethyl instead of methyl.

Table 13

Table 13 consists of 28 compounds of the general formula (1), where $R_1$ is ethyl, $R_2$ is hydrogen, $R_3$ and $R_4$ are both methyl, $R_5$ is methoxymethyl and X and Y have the values listed in Table 1. Thus compound 1 of Table 13 is the same as compound 1 of Table 1 except that in compound 1 of Table 13 $R_5$ is methoxymethyl instead of methyl. Similarly, compounds 2 to 28 of Table 13 are the same as compounds 2 to 28 of Table 1, respectively, except that in the compounds of Table 13 $R_5$ is methoxymethyl instead of methyl.

Table 14

Table 14 consists of 28 compounds of the general formula (1), where $R_1$ is methyl, $R_2$ is hydrogen, $R_3$ and $R_4$ are both methyl, $R_5$ is methoxymethyl and X and Y have the values listed in Table 1. Thus compound 1 of Table 14 is the same as compound 1 of Table 2 except that in compound 1 of Table 14 $R_5$ is methoxymethyl instead of methyl. Similarly, compounds 2 to 28 of Table 14 are the same as compounds 2 to 28 of Table 2, respectively, except that in the compounds of Table 14 $R_5$ is methoxymethyl instead of methyl.

Table 15

Table 15 consists of 28 compounds of the general formula (1), where $R_1$ is n-propyl, $R_2$ is hydrogen, $R_3$ and $R_4$ are both methyl, and $R_5$ is methoxymethyl and X and Y have the values listed in Table 1. Thus compound 1 of Table 15 is the same as compound 1 of Table 3 except that in compound 1 of Table 15 $R_5$ is methoxymethyl instead of methyl. Similarly, compounds 2 to 28 of Table 15 are the same as compounds 2 to 28 of Table 3, respectively, except that in the compounds of Table 15 $R_5$ is methoxymethyl instead of methyl.

Table 16

Table 16 consists of 28 compounds of the general formula (1), where $R_1$ is n-butyl, $R_2$ is hydrogen, $R_3$ and $R_4$ are both methyl, $R_5$ is methoxymethyl and X and Y have the values listed in Table 1. Thus compound 1 of Table 16 is the same as compound 1 of Table 4 except that in compound 1 of Table 16 $R_5$ is methoxymethyl instead of methyl. Similarly, compounds 2 to 28 of Table 16 are the same as compounds 2 to 28 of Table 4, respectively, except that in the compounds of Table 16 $R_5$ is methoxymethyl instead of methyl.

Table 17

Table 17 consists of 28 compounds of the general formula (1), where $R_1$ is ethyl, $R_2$ is hydrogen, $R_3$ and $R_4$ are both methyl, $R_5$ is tert-butyldimethylsilyloxymethyl and X and Y have the values listed in Table 1. Thus compound 1 of Table 17 is the same as compound 1 of Table 1 except that in compound 1 of Table 17 $R_5$ is tert-butyldimethylsilyloxymethyl instead of methyl. Similarly, compounds 2 to 28 of Table 17 are the same as compounds 2 to 28 of Table 1, respectively, except that in the compounds of Table 17 $R_5$ is tert-butyldimethylsilyloxymethyl instead of methyl.

Table 18

Table 18 consists of 28 compounds of the general formula (1), where $R_1$ is methyl, $R_2$ is hydrogen, $R_3$ and $R_4$ are both methyl, $R_5$ is tert-butyldimethylsilyloxymethyl and X and Y have the values listed in Table 1. Thus compound 1 of Table 18 is the same as compound 1 of Table 2 except that in compound 1 of Table 18 $R_5$ is tert-butyldimethylsilyloxymethyl instead of methyl. Similarly, compounds 2 to 28 of Table 18 are the same as compounds 2 to 28 of Table 2, respectively, except that in the compounds of Table 18 $R_5$ is tert-butyldimethylsilyloxymethyl instead of methyl.

Table 19

Table 19 consists of 28 compounds of the general formula (1), where $R_1$ is n-propyl, $R_2$ is hydrogen, $R_3$ and $R_4$ are both methyl, and $R_5$ is tert-butyldimethylsilyloxymethyl and X and Y have the values listed in Table 1. Thus compound 1 of Table 19 is the same as compound 1 of Table 3 except that in compound 1 of Table 19 $R_5$ is tert-butyldimethylsilyloxymethyl instead of methyl. Similarly, compounds 2 to 28 of Table 19 are the same as compounds 2 to 28 of Table 3, respectively, except that in the compounds of Table 19 $R_5$ is tert-butyldimethylsilyloxymethyl instead of methyl.

Table 20

Table 20 consists of 28 compounds of the general formula (1), where $R_1$ is n-butyl, $R_2$ is hydrogen, $R_3$ and $R_4$ are both methyl, $R_5$ is tert-butyldimethylsilyloxymethyl and X and Y have the values listed in Table 1. Thus compound 1 of Table 20 is the same as compound 1 of Table 4 except that in compound 1 of Table 20 $R_5$ is tert-butyldimethylsilyloxymethyl instead of methyl. Similarly, compounds 2 to 28 of Table 20 are the same as compounds 2 to 28 of Table 4, respectively, except that in the compounds of Table 20 $R_5$ is tert-butyldimethylsilyloxymethyl instead of methyl.

Table 21

Table 21 consists of 28 compounds of the general formula (1), where $R_1$ is ethyl, $R_2$ is hydrogen, $R_3$ and $R_4$ are both methyl, $R_5$ is 1-methoxyethyl and X and Y have the values listed in Table 1. Thus compound 1 of Table 21 is the same as compound 1 of Table 1 except that in compound 1 of Table 21 $R_5$ is 1-methoxyethyl instead of methyl. Similarly, compounds 2 to 28 of Table 21 are the same as compounds 2 to 28 of Table 1, respectively, except that in the compounds of Table 21 $R_5$ is 1-methoxyethyl instead of methyl.

Table 22

Table 22 consists of 28 compounds of the general formula (1), where $R_1$ is methyl, $R_2$ is hydrogen, $R_3$ and $R_4$ are both methyl, $R_5$ is 1-methoxyethyl and X and Y have the values listed in Table 1. Thus compound 1 of Table 22 is the same as compound 1 of Table 2 except that in compound 1 of Table 22 $R_5$ is 1-methoxyethyl instead of methyl. Similarly, compounds 2 to 28 of Table 22 are the same as compounds 2 to 28 of Table 2, respectively, except that in the compounds of Table 22 $R_5$ is 1-methoxyethyl instead of methyl.

Table 23

Table 23 consists of 28 compounds of the general formula (1), where $R_1$ is n-propyl, $R_2$ is hydrogen, $R_3$ and $R_4$ are both methyl, and $R_5$ is 1-methoxyethyl and X and Y have the values listed in Table 1. Thus compound 1 of Table 23 is the same as compound 1 of Table 3 except that in compound 1 of Table 23 $R_5$ is 1-methoxyethyl instead of methyl. Similarly, compounds 2 to 28 of Table 23 are the same as compounds 2 to 28 of Table 3, respectively, except that in the compounds of Table 23 $R_5$ is 1-methoxyethyl instead of methyl.

Table 24

Table 24 consists of 28 compounds of the general formula (1), where $R_1$ is n-butyl, $R_2$ is hydrogen, $R_3$ and $R_4$ are both methyl, $R_5$ is 1-methoxyethyl and X and Y have the values listed in Table 1. Thus compound 1 of Table 24 is the same as compound 1 of Table 4 except that in compound 1 of Table 24 $R_5$ is 1-methoxyethyl instead of methyl. Similarly, compounds 2 to 28 of Table 24 are the same as compounds 2 to 28 of Table 4, respectively, except that in the compounds of Table 24 $R_5$ is 1-methoxyethyl instead of methyl.

Table 25

Table 25 consists of 28 compounds of the general formula (1), where $R_1$ is ethyl, $R_2$ is hydrogen, $R_3$ and $R_4$ are both methyl, $R_5$ is 3-cyanopropyl and X and Y have the values listed in Table 1. Thus compound 1 of Table 25 is the same as compound 1 of Table 1 except that in compound 1 of Table 25 $R_5$ is 3-cyanopropyl instead of methyl. Similarly, compounds 2 to 28 of Table 25 are the same as compounds 2 to 28 of Table 1, respectively, except that in the compounds of Table 25 $R_5$ is 3-cyanopropyl instead of methyl.

Table 26

Table 26 consists of 28 compounds of the general formula (1), where $R_1$ is methyl, $R_2$ is hydrogen, $R_3$ and $R_4$ are both methyl, $R_5$ is 3-cyanopropyl and X and Y have the values listed in Table 1. Thus compound 1 of Table 26 is the same as compound 1 of Table 2 except that in compound 1 of Table 26 $R_5$ is 3-cyanopropyl instead of methyl. Similarly, compounds 2 to 28 of Table 26 are the same as compounds 2 to 28 of Table 2, respectively, except that in the compounds of Table 26 $R_5$ is 3-cyanopropyl instead of methyl.

Table 27

Table 27 consists of 28 compounds of the general formula (1), where $R_1$ is n-propyl, $R_2$ is hydrogen, $R_3$ and $R_4$ are both methyl, and $R_5$ is 3-cyanopropyl and X and Y have the values listed in Table 1. Thus compound 1 of Table 27 is the same as compound 1 of Table 3 except that in compound 1 of Table 27 $R_5$ is 3-cyanopropyl instead of methyl. Similarly, compounds 2 to 28 of Table 27 are the same as compounds 2 to 28 of Table 3, respectively, except that in the compounds of Table 27 $R_5$ is 3-cyanopropyl instead of methyl.

Table 28

Table 28 consists of 28 compounds of the general formula (1), where $R_1$ is n-butyl, $R_2$ is hydrogen, $R_3$ and $R_4$ are both methyl, $R_5$ is 3-cyanopropyl and X and Y have the values listed in Table 1. Thus compound 1 of Table 28 is the same as compound 1 of Table 4 except that in compound 1 of Table 28 $R_5$ is 3-cyanopropyl instead of methyl. Similarly, compounds 2 to 28 of Table 28 are the same as compounds 2 to 28 of Table 4, respectively, except that in the compounds of Table 28 $R_5$ is 3-cyanopropyl instead of methyl.

The compounds of formula (1) may be prepared as outlined in Schemes 1 to 3 below in which X, Y, Z, $R_1$, $R_2$, $R_3$, $R_4$ and $R_5$ have the meanings given above, R is $C_{1-4}$ alkyl, L is a leaving group such as a halide, for example iodide, or an alkyl or aryl sulphonyloxy group, for example methylsulphonyloxy and tosyloxy or a triflate, Hal is halogen, $R_a$ is hydrogen or $C_{1-3}$ alkyl, $R_b$ is hydrogen or $C_{1-3}$ alkyl, provided that the total number of carbon atoms in $R_a$ and $R_b$ do not exceed three, $R_c$ is $C_1$— alkyl, optionally substituted benzyl or optionally substituted thienylmethyl.

Compounds of general formula (1) may be prepared as shown in Scheme 1. Esters of formula (4) can be formed by reaction of pyridinols of formula (2) and compounds of formula (3), where L is a leaving group such as a chlorine or bromine atom, or a mesylate or tosylate group, in the presence of a base such a potassium t-butoxide, in suitable solvent such a t-butanol. The esters of formula (4) can be hydrolysed to acids of formula (7) by treatment with an alkali metal hydroxide, such as sodium hydroxide, in an aqueous alcohol ROH, where R is a $C_{1-4}$ alkyl group at between room temperature and reflux. The acids of formula (5) can be condensed with the amines of formula (6) to give the compounds of general formula (1), using suitable activating reagents such as HOBT (1-hydroxybenztriazole) and EDC N-[3-(dimethylamino) propyl]-N'-ethylcarbodiimide hydrochloride).

As shown in Scheme 2, amines of the general formula (6), wherein $R_2$ is H, correspond to amines of the general formula (10) and may be prepared by alkylation of a silyl-protected aminoalkyne of the general formula (8) using a suitable base, such as n-butyl lithium, followed by reaction with a suitable alkylating reagent $R_5L$, such as an is alkyl iodide, for example, methyl iodide, to form an alkylated compound of the general formula (9). In a similar procedure, a silyl-protected aminoalkyne of the general formula (8) may be reacted with a carbonyl derivative $R_aCOR_b$, for example formaldehyde, using a suitable base, such as n-butyl lithium, to provide an aminoalkyne (9) containing a hydroxyalkyl moiety. The silyl protecting group may then be removed from a compound of the general formula (9) with, for example, an aqueous acid to form an aminoalkyne of the general formula (10). Aminoalkynes of the general formula (10) may be further derivatised, for instance when $R_5$ is a hydroxyalkyl group, for example, by reacting a compound of the general formula (10) with a silylating agent $(R)_3SiCl$, for example t-butyldimethylsilyl chloride, to give a derivative silylated on oxygen of the general formula (10a). In addition, a compound of the general formula (10) may be treated with a base, such as sodium hydride or potassium bis(trimethylsilyl)amide followed by a compound $R_cL$ to give a compound of the general formula (10b). In an alternative sequence, a compound of general formula (9) may be treated with a base, such as sodium or potassium bis(trimethylsilyl)amide, followed by a compound $R_cL$, where L represents a halogen or sulphonate ester such as $OSO_2Me$, or $OSO_2$-4-tolyl, for example ethyl iodide, to give compounds of general formula (11), which after removal of the silyl protecting group, give compounds of general formula (10b).

Compounds of general formula (9), where $R_5$ is for example 3-chloropropyl, can be reacted with a metal cyanide salt, such as sodium cyanide, to give compounds of general formula (13), which can then be hydrolysed, with for example an aqueous acid, to give the amines of general formula (14). Compounds of general formula (9), where $R_5$ is for example 3-chloropropyl, can be hydrolysed, with for example an aqueous acid, to give amines of general formula (12).

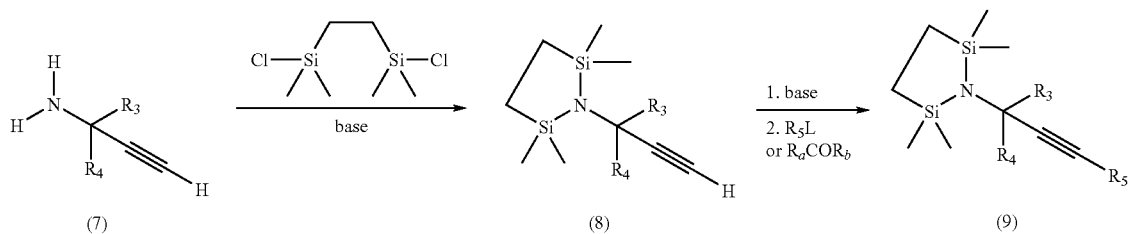

Scheme 2

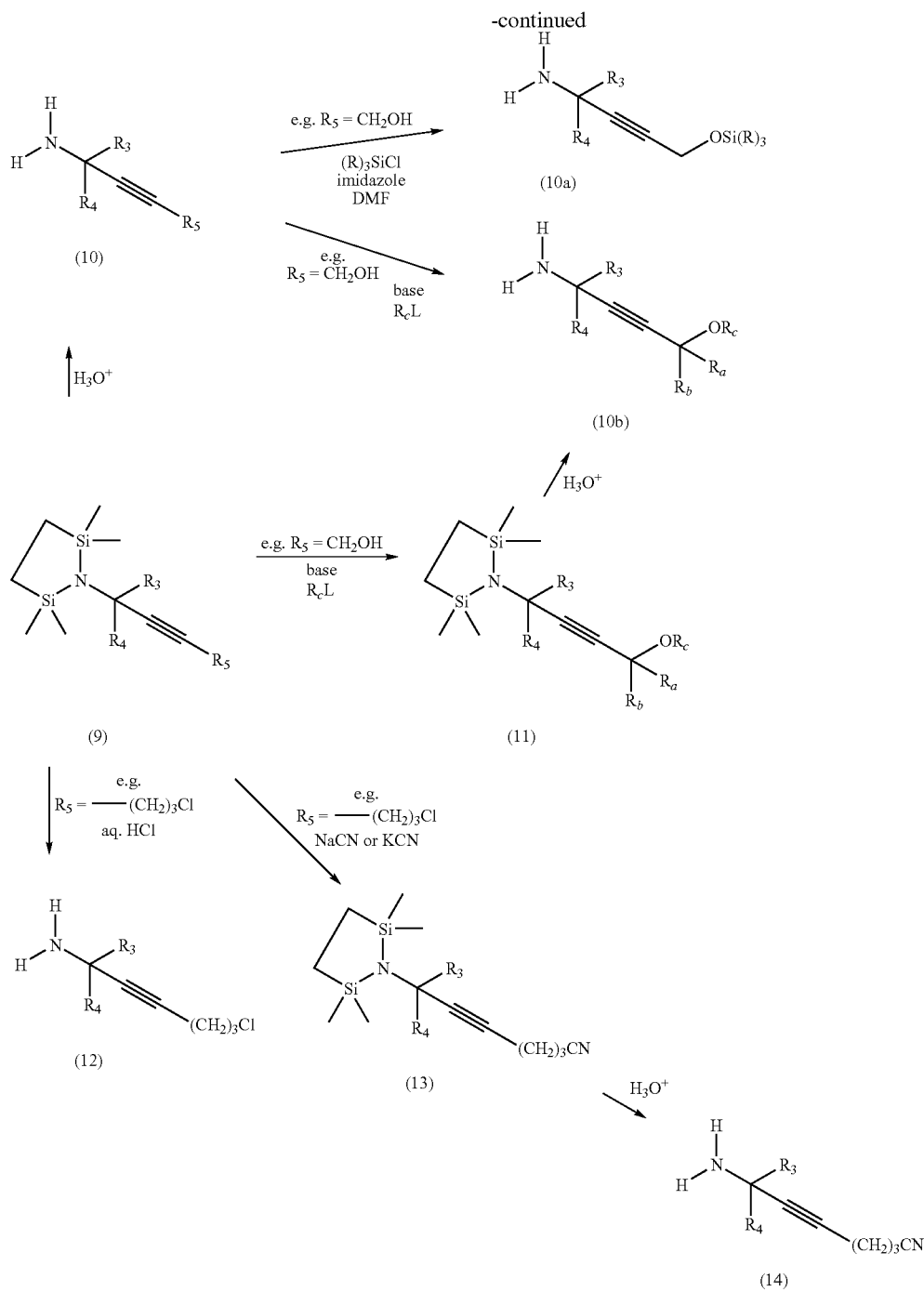

Silyl-protected aminoalkynes of the general formula (8) may be obtained by reacting amines of general formula (7) with 1,2-bis-(chlorodimethylsilyl)ethane in the presence of a suitable base, such as a tertiary organic amine base, for example, triethylamine.

Amines of the general formula (7) are either commercially available or may be prepared by standard literature methods (see, for example, EP-A-0834498).

As shown in Scheme 3, compounds of general formula (1), where $R_5$ is for example 3-chloropropyl, can be reacted with various nucleophiles such as a metal cyanide salt, for example sodium cyanide, to give compounds of general formula (15), with metal alkoxides, for example sodium methoxide, to give compounds of general formula (16), with 1,2,4-triazole in the presence of base such as triethylamine to give compounds of general formula (17), and with metal thioalkoxides, for example sodium methanethiolate, to give compounds of general formula (18). Compounds of general formula (18) can be treated with oxidising agents such as sodium periodate, to give sulphoxides of general formula (19), or with oxidising agents such as m-chloroperbenzoic acid, to give sulphones of general formula (20).

Scheme 3

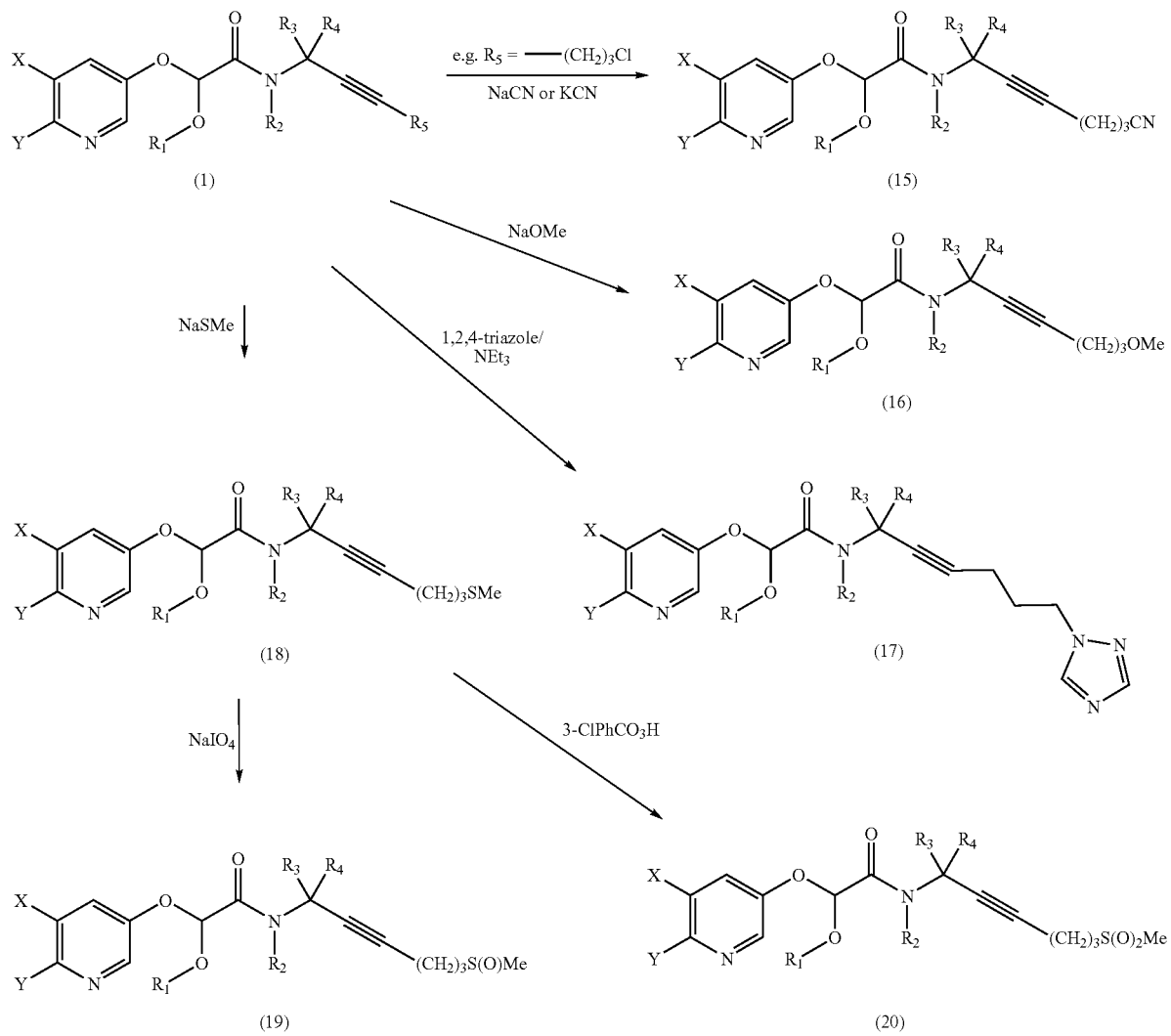

The compounds of formula (1) are active fungicides and may be used to control one or more of the following pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella*

*pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythlium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostoma piceae, Penicillium* spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

The compounds of formula (1) show particularly good activity against the Oomycete class of pathogens such as *Phytophthora infestans, Plasmopara* species, e.g. *Plasmopara viticola* and *Pythium* species e.g. *Pythium ultimum*.

A compound of formula (1) may move acropetally, basipetally or locally in plant tissue to be active against one or more fungi. Moreover, a compound of formula (1) may be volatile enough to be active in the vapour phase against one or more fungi on the plant.

The invention therefore provides a method of combating or controlling phytopathogenic fungi which comprises applying a fungicidally effective amount of a compound of formula (1), or a composition containing a compound of formula (1), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (1) are preferably used for agricultural, horticultural and turfgrass purposes in the form of a composition.

In order to apply a compound of formula (1) to a plant, to a seed of a plant, to the locus of the plant or seed or to soil or any other growth medium, a compound of formula (1) is usually formulated into a composition which includes, in addition to the compound of formula (1), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (1). The composition is generally used for the control of fungi such that a compound of formula (1) is applied at a rate of from 0.1 g to 10 kg per hectare, preferably from 1 g to 6 kg per hectare, more preferably from 1 g to 1 kg per hectare.

When used in a seed dressing, a compound of formula (1) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (1) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (1).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (1).

Dustable powders (DP) may be prepared by mixing a compound of formula (1) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (1) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (1) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (1) and one or more powdered solid diluents or carriers, or from pre-formed blank granules by absorbing a compound of formula (1) (or a solution thereof, in a suitable agent) in a porous granular material (such as pumice, attapulgite clays, fuller's earth, kieselguhr, diatomaceous earths or ground corn cobs) or by adsorbing a compound of formula (1) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (1) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (1) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (1) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (1) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (1). SCs may be prepared by ball or bead milling the solid compound of formula (1) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (1) may be dry milled and added to water, containing agents hereinbefore described, to produce the desired end product.

Aerosol formulations comprise a compound of formula (1) and a suitable propellant (for example n-butane). A compound of formula (1) may also be dissolved or dispersed in a suitable medium (for example water or a water miscible liquid, such as n-propanol) to provide compositions for use in non-pressurised, hand-actuated spray pumps.

A compound of formula (1) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (1) and, optionally, a carrier or diluent therefor. The polymeric shell may be produced by either an interfacial polycondensation reaction or by a coacervation procedure. The compositions may provide for controlled release of the compound of formula (1) and they may be used for seed treatment. A compound of formula (1) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (1)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (1)).

A compound of formula (1) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (1) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (1) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (1) (for example 0.0001 to 10%, by weight) depending upon the purpose for which they are to be used.

A compound of formula (1) may be used in mixtures with fertilisers (for example nitrogen-, potassium- or phosphorus-containing fertilisers). Suitable formulation types include granules of fertiliser. The mixtures suitably contain up to 25% by weight of the compound of formula (1).

The invention therefore also provides a fertiliser composition comprising a fertiliser and a compound of formula (1).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (1) alone. Further the other fungicide may have a synergistic effect on the fungicidal activity of the compound of formula (1).

The compound of formula (1) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (1); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) propionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-S-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N-([methyl(methyl-thioethylideneaminooxycarbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothal-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzaamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

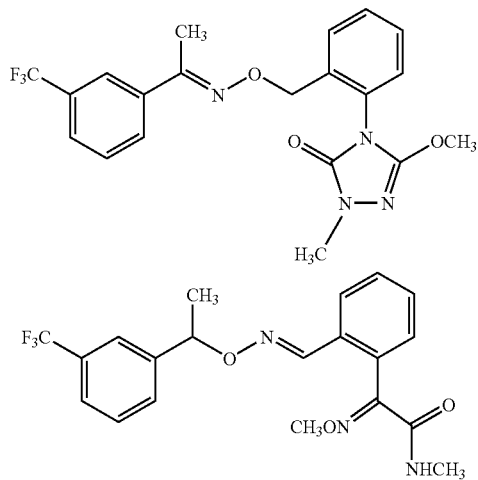

The compounds of formula (1) may be mixed with soil, peat or other rooting media for the protection of plants against seed-borne, soil-borne or foliar fungal diseases.

Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:

ml = milliliters
g = grammes
ppm = parts per million

-continued $M^+$ = mass ion
s = singlet
br s = broad singlet
d = doublet
dd = double doublet
DMSO = dimethylsulphoxide
NMR = nuclear magnetic resonance
HPLC = high performance liquid chromatography
t = triplet
q = quartet
m = multiplet
ppm = parts per million

EXAMPLE 1

This Example illustrates the preparation of 2-(5-chloropyridyl-3-oxy)-2-(ethoxy)-N-(2-methylpent-3-yn-2-yl) acetamide (Compound No. 1, Table 1)

Step 1

Potassium t-butoxide (2.4 g) was dissolved in t-butyl alcohol (130 ml). The mixture was stirred for 30 minutes at room temperature and then 5-chloropyridinol (2.0 g) added, followed by ethyl 2-chloro-2-ethoxyacetate (3.14 g, 90% pure), and a catalytic amount of potassium iodide (0.005 g). The reaction became pink orange and potassium chloride precipitated. The mixture was then stored for 18 hours and poured into water and extracted with chloroform. The organic phase was separated, washed with brine, dried over magnesium sulphate and evaporated to give a colourless oil which was purified by flash column chromatography on silica gel (40-60) eluting with using ethyl acetate/hexane (1:4) to give the required product as a colourless oil (3.08 g).
$^1$H NMR (CDCl$_3$) δ ppm: 1.27 (3H,t); 1.31 (3H,t); 3.75 (1H, m); 3.83 (1H,m); 4.30(2H,q); 5.33 (1H,s); 7.46 (1H,t); 8.30 (1H,d); 8.35 (1H,d).

Step 2

To ethyl 2-(5-chloropyridyl-3-oxy)-2-(ethoxy)acetate (0.45 g) in methanol (5 ml) at room temperature was added a solution of sodium hydroxide (0.076 g) in water (1.5 ml). The reaction was stirred for 5 minutes, the methanol evaporated and the residue was washed with ethyl acetate. The aqueous fraction was then acidified with hydrochloric acid and extracted with ethyl acetate. The ethyl acetate fraction was dried over magnesium sulphate and evaporated to give 2-(5-chloropyridyl-3-oxy)-2-(ethoxy)acetic acid as a pale yellow gum (0.40 g), which was used without further purification.
$^1$H NMR (CDCl$_3$) δ ppm: 1.30 (3H,t); 3.78 (1H,m); 3.90 (1H,m); 5.59 (1H,s); 7.60(1H,s); 8.30 (1H,d), 8.40 (1H,d).

Step 3

Triethylamine (0.30 ml) was added to a stirred solution of 4-amino-4-methyl-pent-2-yne hydrochloride (0.231 g) in DMF (8 ml) giving a white suspension. 2-(5-Chloropyridyl-3-oxy)-2-(ethoxy)acetic acid (0.40 g) was added followed by a catalytic amount of 1-hydroxybenzotriazole (0.005 g) and N-(3-dimethylaminopropyl)-N'-ethylcarbodiimide hydrochloride (0.332 g). The white suspension was stirred at room temperature for 18hours, water added and the aqueous phase extracted with ethyl acetate. The organic phase was washed with water, saturated sodium bicarbonate and then brine, dried over magnesium sulphate, and evaporated to give a yellow oil, which was purified by flash column chromatography on silica gel (40-60) eluting with ethyl acetate/hexane (1:4) to give the required product as a colourless oil (0.130 g).
$^1$H NMR (CDCl$_3$) δ ppm: 1.30 (3H,t); 1.62 (3H,s); 1.63 (6H,s); 3.67 (1H, m); 1.82(3H,s); 3.70 (1H,m); 3.88 (1H, m); 5.32 (1H,s); 6.71 (1H, brs); 7.53 (1H,dd); 8.29 (1H,d); 8.35 (1H,d).

TABLE 29

| Compound No. | Table No. | (Solvent): $^1$H NMR chemical shifts in ppm from TMS |
|---|---|---|
| 1 | 1 | (CDCl$_3$): 1.30 (3H,t); 1.62 (3H,s); 1.63 (6H,s); 3.67 (1H, m); 1.82 (3H,s); 3.70 (1H,m); 3.88 (1H,m); 5.32 (1H,s); 6.71 (1H, bs); 7.53 (1H,dd); 8.29 (1H,d); 8.35 (1H,d). |
| 1 | 9 | (CDCl$_3$): 1.30 (3H, t), 1.61 (3H, s), 1.67 (3H, s), 3.58 (1H, bs), 3.75 (1H, m), 3.92 (1H, m), 4.23 (2H, s), 5.35 (1H, s), 6.74 (1H, bs), 7.47 (1H, m), 8.26 (1H, d), 8.34 (1H, d). |
| 1 | 17 | (CDCl$_3$): 0.12 (6H,s); 0.91 (9H,s); 1.29 (3H,t); 1.64 (3H,s); 1.66 (3H,2); 3.70 (1H,m); 3.88 (1H,m); 4.33 (2H,s); 5.31 (1H,s); 6.71 (1H,bs); 7.51 (1H,t); 8.28 (1H,d); 8.35 (1H,d). |
| 1 | 13 | (CDCl$_3$): 1.29 (3H,t); 1.66 (6H,s); 3.36 (3H,s); 3.70 (1H,m); 3.88 (1H,m); 4.11 (2H,s); 5.33 (1H,s); 6.71 (1H,bs); 7.52 (1H,t); 8.28 (1H,d); 8.35 (1H,d). |

EXAMPLE 2

This Example illustrates the fungicidal properties of compounds of formula (1). The compounds were tested in a leaf disk assay, with methods described below. The test compounds were dissolved in DMSO and diluted into water to 200 ppm.

*Erysiphe graminis* f. sp. *hordei* (barley powdery mildew): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Erysiphe graminis* f. sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Septoria tritici* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

The following compounds gave greater than. 60% control of disease (number of compound first, followed by table number in brackets):

*Plasmopara viticola*, compounds 1 (1), 1 (9), 1 (13); *Phytophthora infestans*, compounds 1 (1), 1 (9), 1 (17); *Erysiphe graminis* f. sp. *hordei*, compounds 1 (1); *Erysiphe graminis* f. sp. *tritici*, compound 1 (13); *Septoria tritici* compound 1 (9).

The invention claimed is:

1. A compound of the general formula (1):

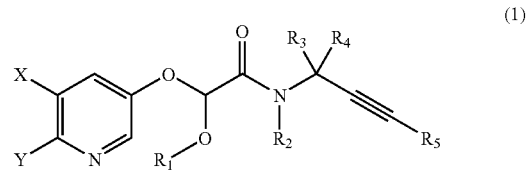

(1)

or the corresponding pyridine N-oxide, wherein X is chloro or bromo and Y is H; R$_1$ methyl, ethyl, n-propyl, n-butyl; R$_2$ is H; R$_3$ and R$_4$ are both methyl; and R$_5$ is H, methyl, hydroxymethyl, methoxymethyl, 1-methoxyethyl, tert-butyldimethylsilyloxymethyl, 3-methylthiopropyl, 3-methanesulphinylpropyl or 3-methanesulphonylpropyl.

2. A fungicidal composition comprising a fungicidally effective amount of a compound of formula (1) as defined in claim 1.

3. A method of combating or controlling phytopathogenic fungi which comprises applying a fungicidally effective amount of a compound of formula (1) as defined in claim 1 to a plant, to a seed of a plant, to the locus of the plant or seed or to soil or any other plant growth medium.

* * * * *